United States Patent [19]

Schmitt et al.

[11] Patent Number: 5,040,539
[45] Date of Patent: Aug. 20, 1991

[54] PULSE OXIMETER FOR DIAGNOSIS OF DENTAL PULP PATHOLOGY

[75] Inventors: Joseph M. Schmitt, Rockville, Md.; Richard L. Webber, Birmingham, Ala.; Elijah C. Walker, Silver Spring, Md.

[73] Assignee: The United States of America, Washington, D.C.

[21] Appl. No.: 350,908

[22] Filed: May 12, 1989

[51] Int. Cl.⁵ .................................... A61B 5/02
[52] U.S. Cl. ............................ 128/633; 128/665
[58] Field of Search .................. 128/633, 664, 665; 433/215, 229

[56] References Cited

U.S. PATENT DOCUMENTS

| Re. 31,815 | 1/1985 | Alfano | 128/665 |
| 3,638,640 | 2/1972 | Shaw | 128/633 |
| 3,648,685 | 3/1972 | Hepp et al. | 128/665 |
| 4,407,290 | 10/1983 | Wilber | 128/633 |
| 4,479,499 | 10/1984 | Alfano | 128/665 |
| 4,564,355 | 1/1986 | Traizer et al. | 128/633 |
| 4,700,708 | 10/1987 | New, Jr. et al. | 128/633 |
| 4,759,369 | 7/1988 | Taylor | 128/664 |
| 4,813,421 | 3/1989 | Baudino et al. | 128/633 |
| 4,836,206 | 6/1989 | Maxwell et al. | 128/633 |
| 4,865,038 | 9/1989 | Rich et al. | 128/665 |
| 4,869,254 | 9/1989 | Stone et al. | 128/633 |

Primary Examiner—Lee S. Cohen
Assistant Examiner—John D. Zele
Attorney, Agent, or Firm—Cushman, Darby & Cushman

[57] ABSTRACT

A non-invasive device which determines the pulp oxygenation level of a tooth and the vitality of a tooth using multiple-wavelength optical plethysmography. A sensor is shaped to be mounted on a tooth and circuitry for processing a signal from the sensor and supplied from a photosenstive diode is used. The photosensitive diode in the sensor detects light scattered from the tooth which was emitted from red, green, and infrared LEDs. An electrocardiogram (ECG) monitor is provided so as to produce improved detection reliability by synchronous averaging using the occurrence of the R-wave of the ECG as a time marker. Using this approach, a threshold-of-detection criterion can be established based on an average computed over a period to achieve a desired signal-to-noise ratio.

18 Claims, 10 Drawing Sheets

PULSE OXIMETER FOR DIAGNOSIS OF DENTAL PULP PATHOLOGY

FIELD OF THE INVENTION

This apparatus relates to an improvement in diagnosing dental diseases. More particularly, this invention relates to a method and apparatus for providing an objective measurement of the status of the dental pulp of a tooth for diagnostic purposes.

BACKGROUND OF THE INVENTION

Diagnosis of diseases of the dental pulp can prove challenging to the dental practitioner. A tooth may appear normal in standard visual and radiographic examinations, and yet be undergoing a process of chronic degeneration. In other instances, a patient may experience tooth pain caused by acute inflammation of the pulp which later subsides without the necessity of endodontic therapy. As diagnostic tools are few and subjective, clinicians often must extract a tooth with no knowledge of its true pathological condition to avoid the possibility of future complications.

The techniques now employed to detect dental-pulp pathology are based on subjective evaluation of a patient's response to thermal, mechanical or electrical stimuli. A stimulus is applied to the tooth under examination and the patient is asked whether he or she feels a sensation. Problems with these techniques include: 1) the sensation can be unpleasant or painful to the patient, 2) successful stimulation of nerves in the pulp does not exclude the possibility of pulp disease; nerves can still respond even when blood circulation is impaired, 3) stimulating a tooth without also stimulating surrounding gingival tissues or nearby teeth is difficult and, therefore, false-positive errors are likely, and 4) no information concerning the degree or type of pulp pathology is provided because only complete devitalization can be positively identified.

Although various optical devices have been developed previously to assess the condition of teeth, none, as yet, has progressed beyond the prototype stage. Alfano, U.S. Pat. No. 4,290,433, discloses a method for caries detection based upon measurement of the relative luminescence of the tooth crown at two different wavelengths. Unlike the present invention which enables the determination of the condition of the tooth pulp, Alfano's invention only allows measurement of superficial abnormalities in the enamel and dentin layers which comprise the hard tissues of the tooth. Another U.S. patent issued to Hepp et al. identifies transillumination of the teeth and periodontal tissues as a potential diagnostic method, but as this method only allows detection of gross defects in the tooth crown or bony structures to which the teeth are attached, this method cannot be used to determine the conditions of tissue within the pulp cavity.

Maxwell and Webber have suggested a device for determination of tooth vitality based on the measurement of the volume of hemoglobin contained in the pulp cavity of a tooth. One deficiency of this device is its inability to determine vitality in a way that is independent of tooth size and shape. A large vital tooth with a small pulp cavity is likely to yield a different value from that of a small vital tooth containing a pulp cavity of equal volume. Thus, in general, only large changes in hemoglobin content occurring in the same tooth over time are discernible.

SUMMARY OF THE INVENTION

Based on multiple-wavelength optical plethysmography, the device described here is non-invasive and can be manufactured inexpensively in a small, hand-held package. The device can simultaneously measure variables related to the pulsatile flow and oxygenation of blood in the tooth. Detection of flow-related pulsations provides a gross indication of tooth vitality (viable vs. non-viable), and measurement of pulp-tissue oxygen saturation enables various disease states of still-vital teeth (e.g. necrosis and inflammation) to be differentiated. Based on displayed information, the clinician can make a judgment concerning the need for therapeutic intervention.

The main advantage of the present invention over previous technologies is that it enables the clinician to unequivocally determine whether a given tooth is perfused with blood, because changes in optical density synchronous with blood flow, rather than static optical density values, are measured. Blood circulation in a tooth establishes vitality. The device also provides quantitative estimates of the oxygen saturation ($S_{O_2}$) of hemoglobin in the pulp, allowing the clinician to distinguish among various conditions which can lead to degeneration of the tooth. If, for example, the oxygen saturation of blood in a tooth, found to be vital shortly after exposure to blunt trauma, decreases steadily with time, then impairment of the tooth's blood circulation would be suspected. Similarly, acute inflammation could be diagnosed based on altered $S_{O_2}$ values. No other known technology provides comparable diagnostic capabilities.

Other objects, features, and characteristics of the present invention, as well as the methods of operation and functions of the related elements of the structure, and the combination of parts and economies of manufacture, will become apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

A clearer understanding of the present invention can be achieved by studying the following detailed description of the preferred exemplary embodiment together with the drawings in which.

DETAILED DESCRIPTION OF THE PRESENTLY PREFERRED EXEMPLARY EMBODIMENT

Figure 10:
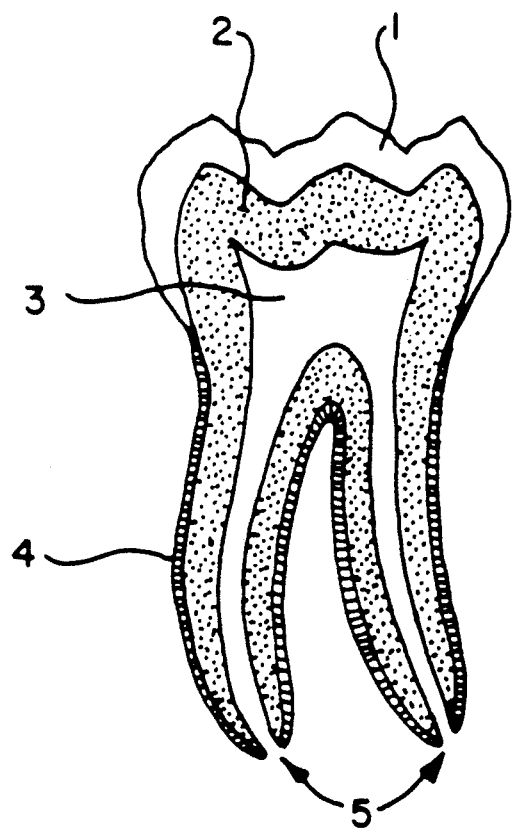
FIG. 10 is a cross section of an adult human tooth.

A cross-sectional view of an adult human tooth (molar) is shown in FIG. 10. The outermost layers of the tooth are composed of hard, bone-like materials called enamel 1 and dentin 2. The principal inorganic component of both is hydroxyapatite. Dry enamel consists of 99% hydroxyapatite microcrystallites and 1% organic material (mostly keratin-like proteins and glycoproteins); dentin is composed of about 80% hydroxyapatite and 20% organic material (mostly collagen and elastin). Collagen fibers passing from the jaw bone to a layer of cementum 4 at the base of the tooth serve to fix the tooth in its socket.

Nerves and blood vessels enter and exit the pulp chamber 3 via the apical foramen 5, small-diameter holes in the tips of the roots of the tooth. Blood perfusing the dental pulp supplies oxygen, mineral salts, and other nutrients necessary to sustain the activity of odontoblasts and neural tissue associated with the dentin. The morphology of the pulp microvasculature is complex: a dense network of capillaries (close to the dentinal layer) interconnect arterioles and venules which traverse the center of the pulp chamber, thus forming a tree-like microvascular structure. Several investigations have reported considerable heterogeneity of blood flow in the pulp, perhaps resulting from arteriovenous fistules and variations in the diameters of the vessels in different regions.

The volume of the pulp chamber relative to that of the entire tooth varies widely among individuals. It also depends on the type of tooth and age, primarily because dentin is continuously produced throughout life in areas originally occupied by pulpal tissue.

Figure 1:
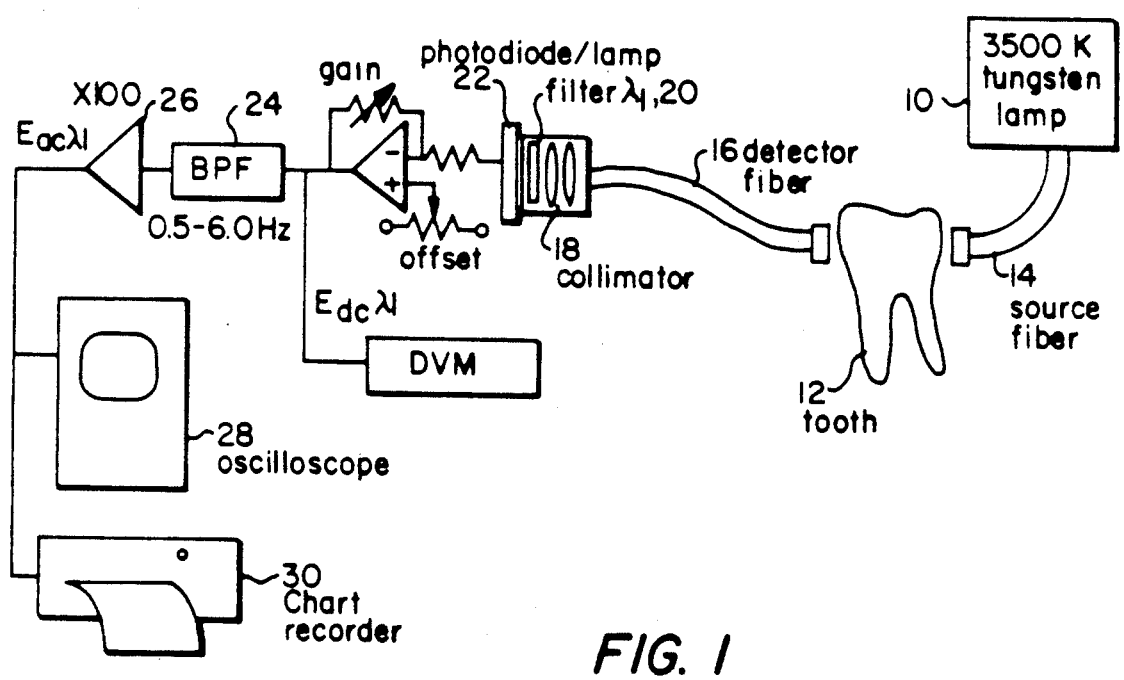
FIG. 1 is a diagram of a transmission spectrophotometer.

In an intact (vital) tooth, blood perfusing the pulp tissue supplies oxygen, mineral salts, and other nutrients necessary to sustain the metabolic activity of odontoblasts and neural tissues. Optical density variations resulting from the periodic fluctuations in the flow of blood to the tooth over the cardiac cycle can be sensed using a transmission spectrophotometer configured as shown in FIG. 1. Light emitted from a source 14 placed on the surface of a tooth undergoes scattering and absorption by the outer layers of the tooth comprised of enamel and dentin. Some of the photons that enter the soft tissue in the pulp cavity are scattered and absorbed by red blood cells, and a fraction of the forward-scattered light is captured by the detector 16. Small changes in the absorption and scattering coefficients of the pulp tissue caused by a transient redistribution of red blood cells within the pulp cavity during systole results in a reduction in the light flux captured by the detector 16. In this manner, pulsatile blood flow in the tooth is detectable as a transient decrease in the received light intensity (i.e. increase in optical density) synchronous with contractions of the heart. The measurement principles are similar to those of finger photoplethysmography, except that the transient increase in optical density of the tooth during systole is probably not caused by an increase in tissue blood volume, because the pulp is contained in a rigid, essentially incompressible cavity.

Figure 2:
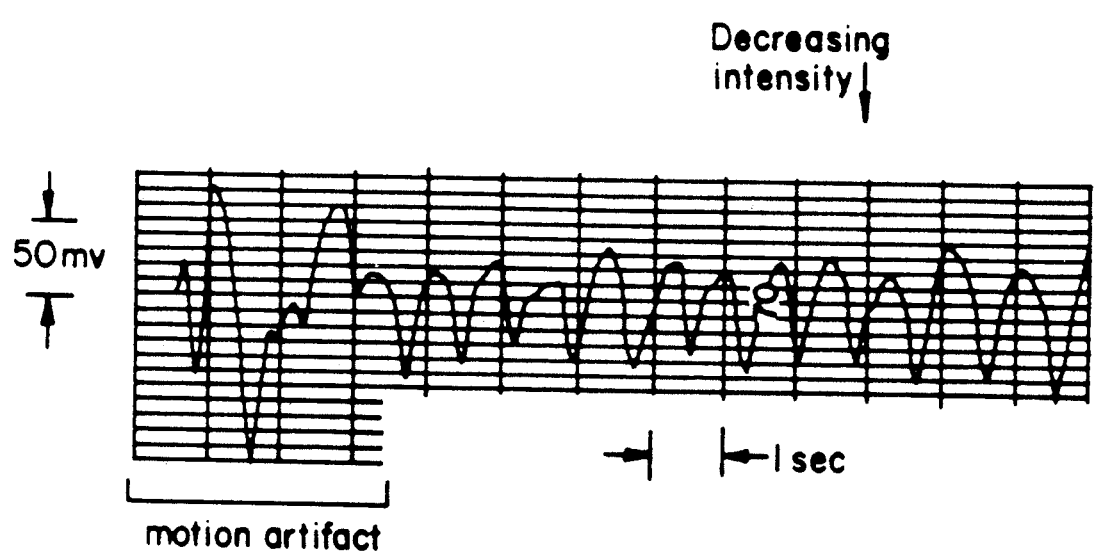
FIG. 2 is a sample pulsatile intensity waveform.

FIG. 2 is an example of a recording of the pulsatile intensity waveform (hereafter referred to as the "tooth pulse plethysmogram" or "tooth PPG") measured from a lower molar of a 29 year-old male. A laboratory spectrophotometer configured as shown in FIG. 1 was used to obtain the recording. Output from the pictured arrangement can be seen on oscilloscope 28 or chart recorder 30.

FIG. 1 shows the buccal aspect of the tooth 12 illuminated with broadband ("white") light from a tungsten-halogen lamp 10 transmitted through a bundle of optical fibers 14. Scattered light is captured by a detector fiber 16 bundle placed on the lingual aspect of the tooth 12 is collimated by collimator 18 before transmission through an interference filter 20 which transmits wavelengths in a 10 nm band centered at 575 nm. A silicon photodiode-amplifier combination 22 (transresistance = 20 M$\Omega$) produces a voltage proportional to the filtered light intensity. To derive a signal proportional to the pulsatile component of the scattered intensity, the output voltage of the photoamplifier 22 is bandpass filtered (0.5–6.0 Hz passband) by filter 24 and amplified ($\times 100$) by amplifier 26.

Figure 3:
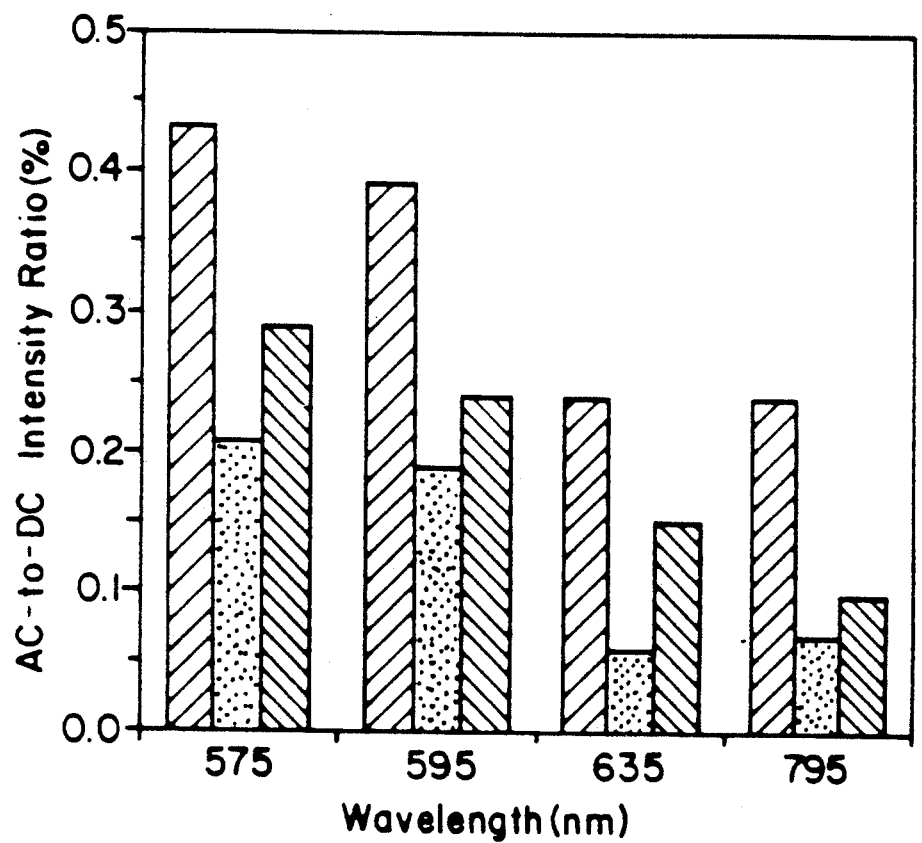
FIG. 3 is a graph showing the experimental results' dependence on wavelength.

As shown by the experimental results in FIG. 3, sensitivity to the flow-related intensity variations, expressed in terms of the ratio of the amplitudes of the pulsatile ('AC') and non-varying ('DC') components of the photoamplifier output signal, depends on the wavelength at which the intensity is measured. Sensitivity is greatest at wavelengths in the green-orange wavelength band (540–600 nm) where the sum of the scattering and absorption coefficients of oxygenated whole blood is greatest.

Figure 4:
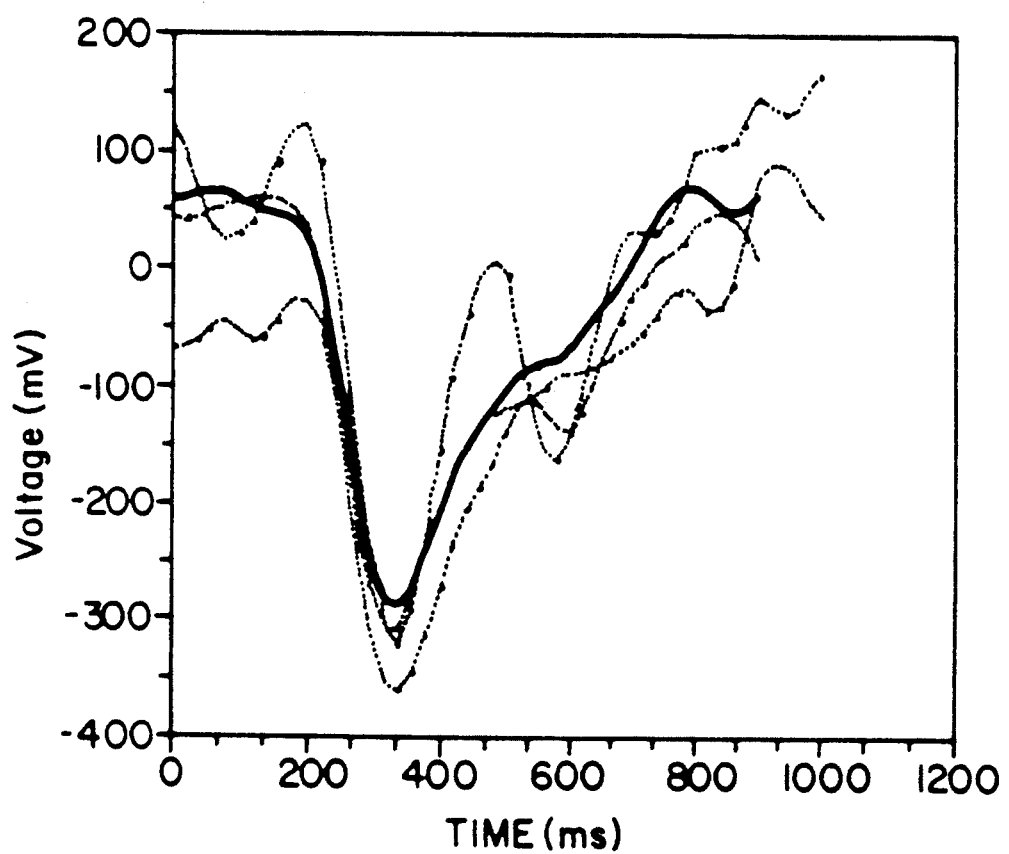
FIG. 4 is an example of a composite waveform formed by averaging noisy tooth PPGs over ten beats.

In some teeth, particularly large teeth with small pulp cavities, the tooth PPG is difficult to detect because motion-induced artifacts and electrical noise generated by the photoelectric conversion process can obscure the PPG signal. To improve detection reliability, synchronous averaging of records using the occurrence of the R-wave of the electrocardiogram (ECG) as a time marker can be performed. An example of composite waveform produced by averaging noisy tooth PPGs over ten beats is shown in FIG. 4. Because motion artifacts and other types of noise evident in the original records are not correlated with the R-wave, these tend to cancel. Using this approach, a threshold-of-detection criterion can be established based on an average computed over a period chosen to achieve a desired signal-to-noise ratio. A longer averaging interval can be employed to increase the level-of-confidence with which a decision regarding tooth vitality can be made.

Figure 5:
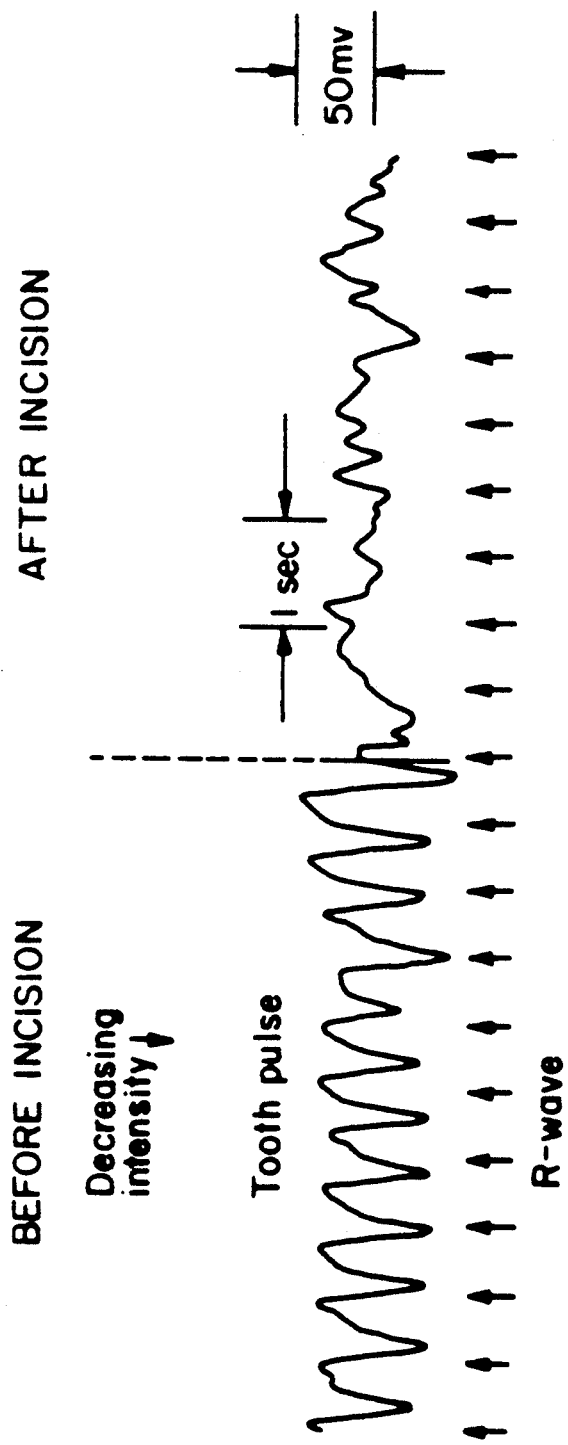
FIG. 5 is an example of a recording from a tooth before and after devitalization.

To establish whether the tooth PPG is completely eliminated when a tooth is devitalized, a controlled study was carried out on the teeth of a dog before and after devitalization. A dog was anesthetized and its ECG was continuously monitored. Intensity signals were measured at 595 nm using the laboratory photometer. A tooth (canine, premolar, or molar) was selected and, while the sensor was held on the tooth, the ECG and AC intensity signals were recorded on a dual-channel chart recorder. After the selected tooth was surgically devitalized by transection of arteries supplying blood to the tooth, recording of the PPG was again attempted. Blood circulation to surrounding gum tissue and other teeth was left intact. This procedure was repeated for each of seven teeth located in both the upper and lower jaw of the dog. In all teeth, flow-correlated intensity variations were eliminated by the surgical devitalization. FIG. 5 is an example of a recording from a tooth before and after devitalization which shows clearly that the synchrony between the ECG R-wave and the AC intensity signal was lost after interruption of the blood circulation to the tooth.

To establish that a tooth is vital, it is sufficient to detect pulsatile optical density variations synchronous with contractions of the heart at any wavelength in the visible-IR spectrum in the manner described above. Additional information about the metabolic status of the tooth can be obtained by measuring the $S_{O2}$ of blood perfusing the pulp tissue using pulse oximetry techniques. In the following paragraphs, a technique is explained which enables estimation of tooth pulp $S_{O2}$ from measurements of diffusely transmitted AC and DC intensities at three wavelengths. The new technique is a modified form of a standard technique employed by commercial pulse oximeters which determine arterial blood $S_{O2}$ from measurements of skin transmittance at two wavelengths.

In earlier investigations, pulse oximetry has been employed to measure the oxygen saturation of blood in tissue capillary beds, According to the following empirical relationship [Yoshiya, 1980]:

$$S_{O2} = A - B \frac{\left(\ln \frac{I_{ac+dc}}{I_{dc}}\right)@\lambda_r}{\left(\ln \frac{I_{ac+dc}}{I_{dc}}\right)@\lambda_{ir}} = A - BR \qquad \text{EQ. 1}$$

In this expression, A and B are constants and $(I_{AC+DC}/I_{DC})@(\lambda)r$ and $(I_{AC+DC}/I_{DC})@(\lambda)ir$ are the ratios of the total intensities (AC+DC) and the non-varying (DC) components of intensities measured at some wavelength in the red (lambda, 630–670 nm) and infrared (lambda$_{ir}$, 800–1000 nm) regions of the spectrum, respectively.

The relationship between R in Eq. 1 and the optical absorption coefficients of blood can be derived using a heuristic description of light propagation in tissue based on the Beer-Lambert law [Yoshiya, 1980]. Consider the two-component model in FIG. 6(a) which shows collimated light at two wavelengths impinging on a slab of tissue. The tissue is divided into 'blood' and 'non-blood' layers 40 and 42, respectively. The blood layer is further divided into a static blood layer of thickness X 44 (containing both venous and arterial blood) and a layer 46 whose thickness, $\Delta$-X, increases as a result of engorgement by arterial blood during systole. Under these conditions, the total intensities received by the detector 48 at lambda, and lambda$_{ir}$ are comprised of both AC and DC components, $$I_{ac+dc,\lambda r} = I_o\exp(-\beta_r T)\exp(-\beta_r' x)\exp(-\beta_r'\Delta x) \qquad \text{EQ.2a}$$

$$I_{ac+dc,\lambda ir} = I_o\exp(-\beta_{ir} T)\exp(-\beta_{ir}' x)\exp(-\beta_{ir}'\Delta x) \qquad \text{EQ.2b}$$

where $I_0$ is the source intensity (assumed to be equal at lambda$_r$ and lambda$_{ir}$), $\beta_r'$ and $\beta_{ir}'$ are absorption coefficients of blood at lambda$_r$ and lambda$_{ir}$, respectively, and $\beta_r$ and $\beta_{ir}$ are absorption coefficients of the bloodless tissues at these same wavelengths.

Dividing the intensities described by the above equation by their respective DC components yields, $$\frac{I_{ac+dc}}{I_{dc}}\bigg|@\lambda_r = \frac{I_o\exp(-\beta_r T)\exp(-\beta_r' x)\exp(-\beta_r'\Delta x)}{I_o\exp(-\beta_r T)\exp(-\beta_r' x)} = \exp(-\beta_r'\Delta x) \qquad \text{EQ. 3a}$$

$$\frac{I_{ac+dc}}{I_{dc}}\bigg|@\lambda_{ir} = \frac{I_o\exp(-\beta_{ir} T)\exp(-\beta_{ir}' x)\exp(-\beta_{ir}'\Delta x)}{I_o\exp(-\beta_{ir} T)\exp(-\beta_{ir}' x)} = \exp(-\beta_{ir}'\Delta x) \qquad \text{EQ. 3b}$$

Taking logarithms and dividing Eq. 3a by Eq. 3b obtains:

$$R = \frac{\left(\ln \frac{I_{ac}+I_{dc}}{I_{dc}}\right)@\lambda_r}{\left(\ln \frac{I_{ac}+I_{dc}}{I_{dc}}\right)@\lambda_{ir}} = \frac{-\beta_r'\Delta x}{-\beta_{ir}'\Delta x} = \frac{\beta_r'}{\beta_{ir}'} \qquad \text{EQ. 4}$$

Alternatively, if the AC component of $I_{AC+DC}$ is small, then $$\ln\left(\frac{I_{ac+dc}}{I_{dc}}\right) \approx \frac{I_{ac}}{I_{dc}} \qquad \text{EQ. 5}$$

so Eq. 4 can be written in a simpler approximate form, $$R = \frac{\beta_r'}{\beta_{ir}'} \approx \frac{\left(\frac{I_{ac}}{I_{dc}}\right)@\lambda_r}{\left(\frac{I_{ac}}{I_{dc}}\right)@\lambda_{ir}} \qquad \text{EQ. 6}$$

The ratio R, which depends only on the ratio of the absorption coefficients of blood at these wavelengths, varies inversely with blood oxygen saturation according to Eq. 1.

Figure 6A:
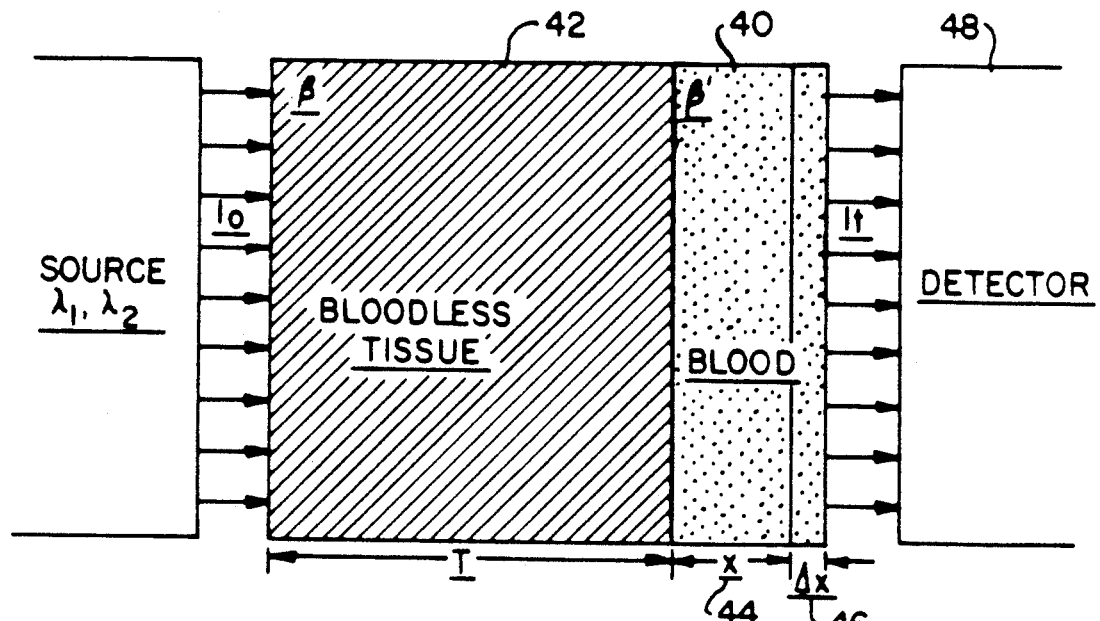
FIG. 6(a) and 6(b) show light impinging on tissue.
Figure 6B:
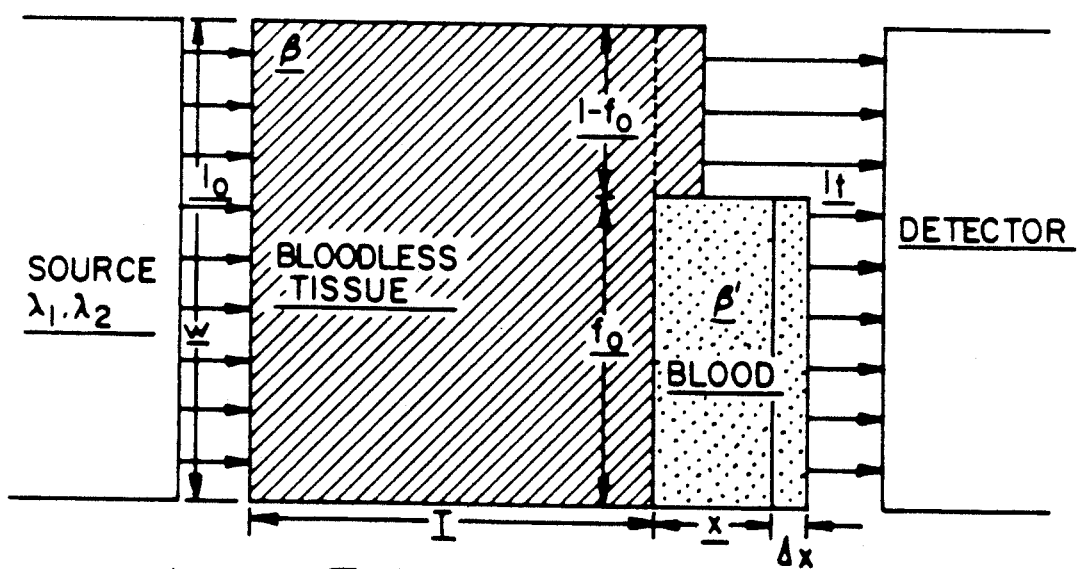

The simple model shown in FIG. 6(a) must be modified as shown in FIG. 6(b) to describe light propagation in the tooth. Because the pulp of the tooth is embedded in a translucent shell, the total intensity captured by the detector is not only comprised of varying and non-varying components attenuated by the blood layer (occupying some fraction $f_0$ of the tissue cross-section), but also of an additive component resulting from direct transmission between the source and detector exclusively through bloodless tissue (enamel and dentin):

$$I_{ac+dc,\lambda r} = I_o[(1-f_0)\exp[-\beta_r(T+W)]+f_0\exp(-\beta_r T)\exp(-\beta_r' x)\exp(-\beta_r'\Delta x)] \qquad \text{EQ7a}$$

$$I_{ac+dc,\lambda ir} = I_o[(1-f_0)\exp[-\beta_{ir}(T+W)]+f_0\exp(-\beta_{ir} T)\exp(-\beta_{ir}' x)\exp(-\beta_{ir}'\Delta x)] \qquad \text{Eq.7b}$$

where T and W are dimensional constants related to the geometry of the tooth. As before, dividing the above two equations by their DC components yields $$\left.\frac{I_{ac+dc}}{I_{dc}}\right|@\lambda r = \frac{I_0[(1-f_0)\exp[-\beta_r(T+W)] + f_0\exp(-\beta_rT)\exp(-\beta_r'x)\exp(-\beta_r'\Delta x)]}{I_0[(1-f_0)\exp[-\beta_r(T+W)] + f_0\exp(-\beta_rT)\exp(-\beta_r'x)]} \quad \text{Eq 8a}$$

$$= \frac{B_1 + f_0\exp(-\beta_rT)\exp(-\beta_r'x)\exp(-\beta_r'\Delta x)}{B_1 + f_0\exp(-\beta_rT)\exp(-\beta_r'x)}$$

$$\left.\frac{I_{ac+dc}}{I_{dc}}\right|@\lambda ir = \frac{I_0[(1-f_0)\exp[-\beta_{ir}(T+W)] + f_0\exp(-\beta_{ir}T)\exp(-\beta_{ir}'x)\exp(-\beta_{ir}'\Delta x)]}{I_0[(1-f_0)\exp[-\beta_{ir}(T+W)] + f_0\exp(-\beta_{ir}T)\exp(-\beta_{ir}'x)]} \quad \text{Eq 8b}$$

$$= \frac{B_2 + f_0\exp(-\beta_{ir}T)\exp(-\beta_{ir}'x)\exp(-\beta_{ir}'\Delta x)}{B_2 + f_0\exp(-\beta_{ir}T)\exp(-\beta_{ir}'x)}$$

where $B_1 = (1-f_0)\exp[-\beta_r(T+W)]$ and $B_2 = (1-f_0)\exp[-\beta_{ir}(T+W)]$ are transmittances through bloodless tissue measured at $\lambda_r$ and $\lambda_{ir}$. It is apparent that the ratios in the above two equations, unlike in the simple case described by Eqs. 3a and 3b, depend on geometrical constants T, W and $f_0$. Therefore, the absorption constants of blood in the tooth cannot be isolated by forming the ratio R as in Eq. 6.

To cancel the effects of the geometrical dependency introduced by the extraneous light path, $B_1$ and $B_2$ must first be subtracted from the numerator and denominator of Eqs. 8a and 8b before forming the ratio. Estimates of the values of $B_1$ and $B_2$ can be obtained by measuring light transmission at a third wavelength ($\lambda_3$), provided that $\lambda_3$ is chosen to satisfy the following criteria: (1) the sum of the absorption and scattering coefficients of enamel and dentin at this wavelength must be similar to that at red and infrared wavelengths, and (2) the absorption coefficients of oxygenated and deoxygenated hemoglobin at $\lambda_3$ must greatly exceed those at $\lambda_r$ and $\lambda_{ir}$ [i.e. $\beta'_{\lambda_3} >> \beta'_r, \beta_{ir}'$ and $\exp(-\beta'_{\lambda_3}x) \to 0$]. Fortunately, absorption and scattering in enamel and dentin have only a weak dependence on wavelength in the visible and near infrared spectral region (for this reason, enamel appears white to the eye), so $\lambda_3$ need only be reasonably close to $\lambda_r$ and $\lambda_{ir}$ to satisfy criterion (1). Criterion (2) is satisfied by wavelengths in the green region of the spectrum (540–570 nm) where the absorption coefficient of oxyhemoglobin is over 20 times greater than that at wavelengths between 630 nm and 1000 nm.

Assuming that criteria (1) and (2) are satisfied at some wavelength $\lambda_3$ in the 540–570 nm wavelength band, then $$B_1 \equiv B_2 \equiv (I_{\lambda_3})/I_{0,\lambda_3} = T_{\lambda_3} \quad \text{Eq. 9}$$

where $B_1$ and $B_2$ are from Eq. 8 and $T_{\lambda_3} = (1-f_0)\exp[-\beta_{\lambda_3}(T+W)]$ is the diffuse transmittance measured at $\lambda_3$. Accordingly, a subtractive correction can be applied to Eq. 8 to cancel the effects of light transmission through the bloodless path, $$\frac{I_{ac+dc,\lambda r} - I_{\lambda_3}}{I_{dc,\lambda r} - I_{\lambda_3}} \cong \exp(-\beta_r'\Delta x) \quad \text{Eq. 10a}$$

$$\frac{I_{ac+dc,\lambda ir} - I_{\lambda_3}}{I_{dc,\lambda ir} - I_{\lambda_3}} \cong \exp(-\beta_{ir}'\Delta x) \quad \text{Eq. 10b}$$

assuming that the source intensity $I_{0,\lambda_3}$ is adjusted to equal that at $\lambda_r$ and $\lambda_{ir}$. Taking logarithms of the above two equations and dividing, the ratio of the absorption coefficients of blood at $\lambda_r$ and $\lambda_{ir}$ is obtained as before in Eq. 4, $$\frac{\ln\left[\frac{I_{ac+dc,\lambda r} - I_{\lambda_3}}{I_{dc,\lambda r} - I_{\lambda_3}}\right]}{\ln\left[\frac{I_{ac+dc,\lambda ir} - I_{\lambda_3}}{I_{dc,\lambda ir} - I_{\lambda_3}}\right]} \cong \frac{\beta_r'}{\beta_{ir}'} \quad \text{Eq. 11}$$

which can be simplified by applying the approximation described by Eq. 5:

$$\frac{\frac{I_{ac,\lambda r}}{I_{dc,\lambda r} - I_{\lambda_3}}}{\frac{I_{ac,\lambda ir}}{I_{dc,\lambda ir} - I_{\lambda_3}}} \cong \frac{\beta_r'}{\beta_{ir}'} \quad \text{Eq. 12}$$

In practice, the transmittances of the hard tissues of the tooth measured at $\lambda_3$, $\lambda_r$ and $\lambda_{ir}$ are not identical because their scattering coefficients decrease slightly with wavelength. Therefore, Eq. 12 can be written more accurately as follows:

$$R' = \frac{\frac{I_{ac,\lambda r}}{I_{dc,\lambda r} - C_0 I_{\lambda_3}}}{\frac{I_{ac,\lambda ir}}{I_{dc,\lambda ir} - C_1 I_{\lambda_3}}} \cong \frac{\beta_r'}{\beta_{ir}'} \quad \text{Eq. 13}$$

where the constants $C_0$ and $C_1$ have been introduced. The values of $C_0$ and $C_1$ are determined mainly by the scattering coefficient vs. wavelength properties of dentin and enamel. For a given set of measurement wavelengths ($\lambda_r$, $\lambda_{ir}$, and $\lambda_3$), $C_0$ and $C_1$ are nearly independent of tooth size and shape.

Finally, by replacing R in Eq. 1 by R', an expression from which the oxygen saturation of blood in the tooth pulp can be estimated from measurements of R' is obtained:

$$So_2 = A - BR' \quad \text{Eq. 14}$$

Figure 7:
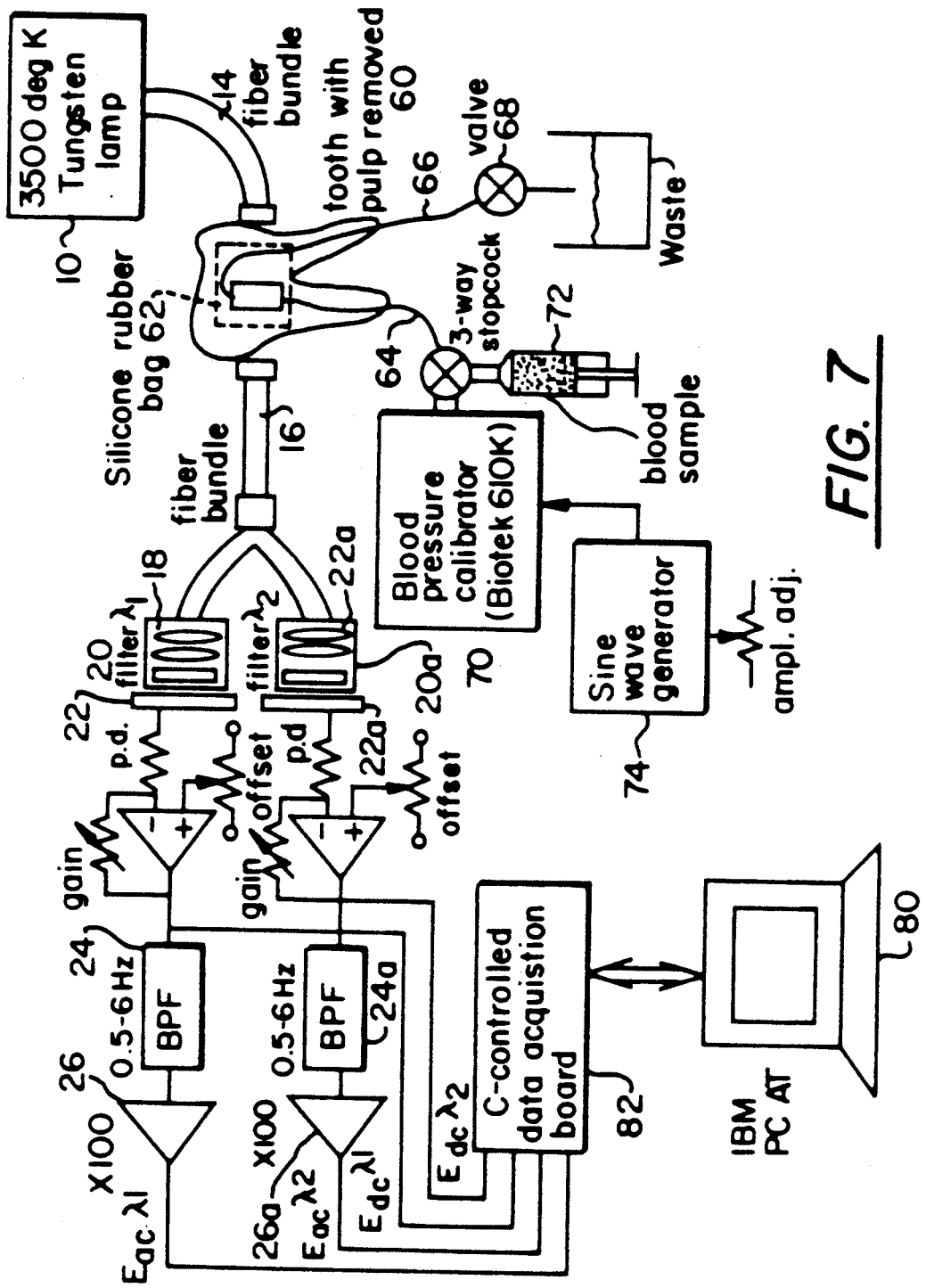
FIG. 7 is a diagram of a tooth PPG simulator.

Experiments were carried out in vitro using the apparatus shown in FIG. 7 to test the validity of the relationship between measured R' values and the oxygen saturation of blood in tooth models.

A model of a tooth with a pulsating dental pulp was prepared by hollowing the central portion of an extracted molar 60 and inserting a thin-walled silicone rubber bag 62 connected to two tubes 64, 66 passing through the apical foramen. During normal operation, the bag and tubing were completely filled with blood, the valve 68 at the end of one of the tubes was closed, and pressure variations generated by an electronic blood pressure calibrator 70 were conducted through the other tube to the bag. In this manner, the amplitude and rate of the volume changes of the blood-filled bag could be controlled by the electrical waveform 74 at the input of the calibrator. Human blood was reconstituted from packed cells and samples 72 having different oxygen saturations were prepared using a Fisher/IL 237 tonometer. The hematocrit of the blood, determined by measuring the packed-cell fraction in capillary-tube samples after centrifugation, was adjusted to 42% by adding isotonic saline. The hemoglobin oxygen saturation of the tonometered blood was measured by a spectrophotometric oximeter (IL 282, Instrumentation Laboratories). In each experiment, samples with oxygen saturations ranging from 45 to 100 percent were prepared and stored on ice in separate syringes before use.

After one of the samples was injected into the simulator, the pressure calibrator was activated, and voltages from the photometer corresponding to the DC and AC components of the diffusely transmitted intensities at 660 nm and 800 nm were digitized at a 50 Hz rate for a period of 10 seconds. This procedure was repeated for each of the remaining samples. Average values of the peak-to-peak ($E_{AC}$) and steady-state ($E_{DC}$) voltages proportional to the AC and DC intensities at 660 nm and 800 nm were computed off-line by a computer 80 equipped with a data acquisition board 82. R' in Eq. 14, with $C_0=1.18$ and $C_1=1.36$ (determined experimentally), was correlated with the measured oxygen saturation of the blood samples. FIG. 7 shows two sets of apparatus connected together, one for each wavelength. The corresponding pieces of the equipment for the second wavelength are denoted by a number followed by an (a) to differentiate those parts from similar parts for wavelength 1.

Figure 8:
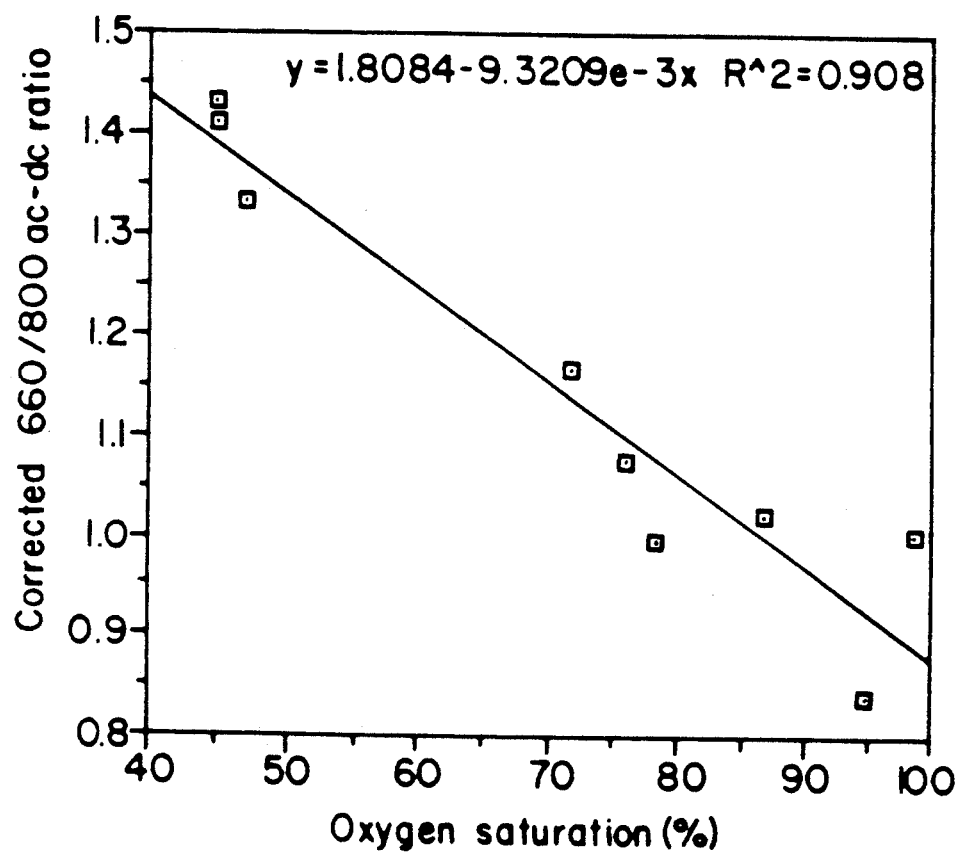
FIG. 8 is a plot of typical experimental results.

Results of a typical experiment are shown in FIG. 8. Correlation between the $So_2$ of the blood in the simulated pulp of the tooth model and the corrected 660/800 nm AC-DC ratio R' exceeded 0.8 in all experiments. The R' vs. $So_2$ calibration curve was not significantly altered by the placement of the source and detector fiber apertures on the surface of the tooth model. Based on the sensitivity and errors of this measurement scheme observed in vitro, It is believed that oxygen saturation changes as small as 10% will be resolvable in actual teeth.

Figure 9:
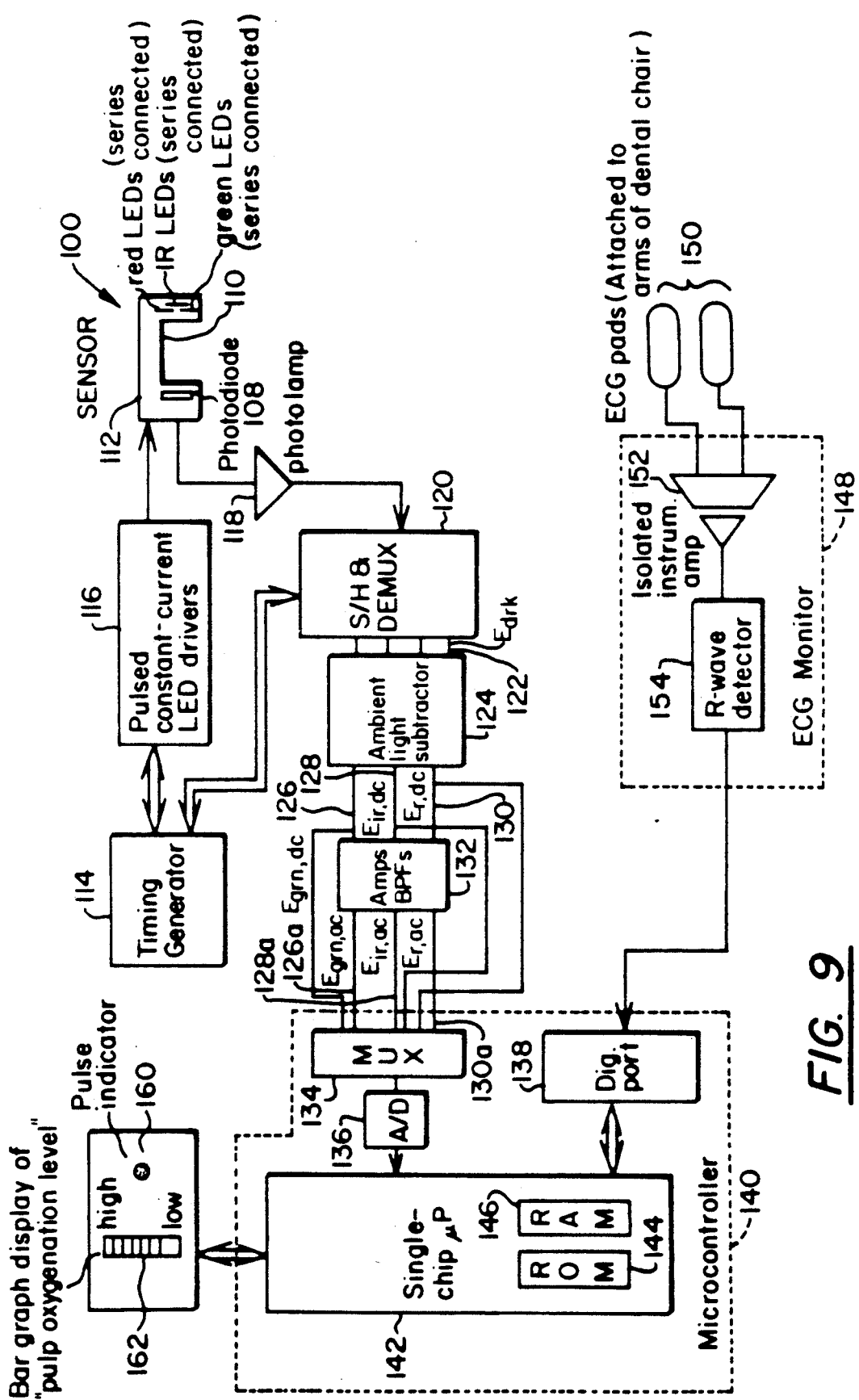
FIG. 9 is a block diagram of the main components of the tooth pulp oximetry system for use in dental clinics.

Referring to FIG. 9, the main components of the tooth-pulp oximetry system for applications in the dental clinic will now be described.

The key element of the system is a sensor 100 containing three sets of light-emitting diodes (LEDs) 102, 104, and 106 and a light detector (for instance, a photosensitive diode) 108. The sensor 100 preferably has a U-shaped configuration, of a shape to facilitate placement on molars and premolars. Those of ordinary skill in the art will recognize that the shape can be modified to fit on incisors as well. The LEDs 102, 104 and 06 and photosensitive diode 108 are preferably mounted on substrates imbedded within U-shaped molded plastic package 112, the inside of which is preferably coated with a black-foam insert 110 which conforms to the shape of a tooth and provides a tight mechanical coupling. Insert 110 should be easily removable and replaceable with a clean insert for successive patients. Such an insert also serves as a light block, preventing stray light from impinging on gingival tissues at the base of the tooth. Package 112 allows the patient to bite down so as not to allow any movement of sensor 100. LEDs of the same wavelength; i.e. red LEDs 102 (peak wavelength=660 nm), infrared LEDs 104 (peak wavelength=880 nm), and green LEDs 106 (peak wavelength=565 nm); may be connected in series to increase the light intensity. The actual number of LEDs of each wavelength depends upon the type of LEDs in use. A lens system (not shown) captures and collimates the light emitted by the LEDs, thereby forming a single, well-defined source aperture.

The LEDs are activated rapidly in sequence by timing generator 114 and pulse drivers 16. The LEDs are activated so as to allow nearly simultaneous measurement of scattered intensity at the different wavelengths of emission of the three sets of LEDs 102, 104 and 106. The peak current is feedback-regulated to maintain a constant source intensity. The photosensitive diode 108 produces a current proportional to the received scattered light intensity, which is amplified and converted to a current by photoamplifier 118. Sample-and-hold and demultiplexing circuitry 120 separates signals corresponding to the intensities at three emission wavelengths and the intensity of ambient light (measured when all LEDs are off) and denoted by $E_{drk}$ 122 from one another. Ambient light subtractor 124 determines the difference between the scattered and ambient light intensity signals.

Three DC signals; $E_{grn,DC}$ 126, $E_{ir,DC}$ 128, and $E_{r,DCi}$ exit subtraction circuitry 124. The DC signals are split, with one branch passing through amplification/band pass filter circuitry 132 and the second branch entering the multiplexer 134 of microcontroller 140. Three AC signals; $E_{grn,AC}$ 126(a), $E_{ir,AC}$ 128(a), and $E_{r,AC}$ 130(a) leave amplification/bandpass circuitry 132.

The microcontroller 140 further comprises A/D converter 136, digital entry port 138, and microprocessor 142. The microprocessor 142 is of the single chip type and includes both ROM 144 and RAM 146 as internal elements. Microcontroller 140 is programmed to detect the presence of the tooth PPG and to estimate pulp oxygenation level. The presence or absence of the tooth PPG is determined by analysis of the bandpass filtered and amplified intensity signal $E_{grn,AC}$. The analog intensity signals $E_{r,DC}$, $E_{ir,DC}$, $E_{grn,DC}$, $E_{r,AC}$, and $E_{ir,AC}$ are digitized and processed to obtain peak-to-peak and average DC intensity values from which $So_2$ is computed according to Equation 14.

To acquire more reliable detection of the tooth PPG, an Electrocardiogram monitor 148 is provided. Monitor 148 provides a means for acquiring a two-lead ECG from the patient. The device uses software-controlled synchronous averaging. Contact to the patient's skin can usually be made by conductive pads 150 attached to the arms of a dental chair. When a patient lightly grasps the arms of the chair, monitor 148 produces a digital pulse concurrent with the R-wave of the patient's ECG. Signal and ground isolation ensure that the patient is not shocked. ECG monitor 148 produces these pulses using amplification circuitry 152 and R-wave detector 154.

To improve measurement precision of the $So_2$ value, synchronous averaging using the R-wave pulse as a reference is performed by the software. The software algorithm dynamically adjusts the length of the averaging interval to achieve a predetermined signal-to-noise ratio. The gain and slope constants that characterize the $So_2$ vs. R' curve are stored in memory, and these values are changed to accommodate different sensor configurations.

Two displays labelled "pulse" and "pulp oxygenation level", 160 and 162 respectively, display information regarding the status of the pulp to the operator. If a tooth is vital, "pulse" indicator 160 flashes every time the heart contracts. An unlit "pulse" indicator signifies a non-vital tooth or an undetectable pulse. A sufficiently strong PPG signal will cause the computed oxygenation level to be displayed on bar graph 162.

While the invention has been described in connection with what is considered to be the most practical and preferred embodiment, it is to be understood that the invention is not limited to the disclosed embodiment. For instance, although LEDs are disclosed as the light source though any equivalent light source could be used. By using a different detector than the photosensitive diode, different wavelength LEDs could be required. Similarly, discrete calculation circuitry could be used in place of microcontroller 140. All such modifications and equivalent arrangements are intended to be included within the spirit and scope of the appended claims.

What is claimed is:

1. Apparatus for detecting vitality of a tooth and measuring variables related to oxygenation and blood flow in said tooth comprising:

a sensor having a housing shaped for placement on said tooth, said housing including a first light emitting diode for emitting light in a red section of the spectrum, a second light emitting diode for emitting light in an infrared section of the spectrum and a third light emitting diode for emitting light in a green section of the spectrum and a photosensitive diode means for receiving light scattered from the emitted light and producing a light reception signal indicative of the intensity levels of said scattered light; and processing means, receiving said light reception signal, for processing said light reception signal and outputting pulp oxygenation level information about said tooth as well as determining pulsatile flood flow from said light reception signal, said information being based on dynamic intensity levels associated with said scattered light.

2. Apparatus as in claim 1, wherein said housing is a substantially U-shaped packaging made of molded plastic and said sensor further includes a removable interior coating for the U-shaped packaging of a material which conforms to the shape of said tooth to provide tight mechanical and optical coupling.

3. Apparatus as in claim 2, wherein said removable interior coating is black in color.

4. Apparatus as in claim 1, wherein said first, second and third light emitting diodes each include a plurality of diode devices in series.

5. Apparatus according to claim 1, wherein said processing means includes means for determining a difference between first, second and third components of the reception signal of said received light and a fourth component of a signal from ambient light and then outputting a first-dc, second-dc, and third-dc signal.

6. Apparatus as in claim 5, wherein said processing means further comprises means for separating each of said first-dc, second-dc, and third-dc signals into a DC signal component and an AC signal component.

7. Apparatus as in claim 6, wherein said processing means further comprises:

means for receiving said AC and DC signal components; and a microprocessor including a RAM and a ROM.

8. Apparatus as in claim 1, further comprising a display unit connected to the processing means including:

a pulse indicator means for flashing when a patient's heart contracts and the tooth is vital; and a bar graph display means for displaying said pulp oxygenation level.

9. Apparatus as in claim 1 further comprising an electrocardiogram (ECG) monitor for detecting ECG information having a common time-base with said light reception signal, and wherein said processing means includes means for determining a synchronization between said light reception signal and said ECG information.

10. Apparatus as in claim 9, wherein said ECG monitor includes ECG pads for producing a digital pulse concurrent with an R-wave of a patient's ECG.

11. Apparatus as in claim 1 further comprising means for initiating said light emitting diodes to sequentially illuminate.

12. Apparatus for detecting vitality of a tooth and measuring variables related to oxygenation and blood flow in said tooth comprising:

a sensor having a housing shaped for placement on said tooth, said housing including a first light emitting diode for emitting light in a red section of the spectrum, a second light emitting diode for emitting light in an infrared section of the spectrum and a third light emitting diode for emitting light in a green section of the spectrum and a photosensitive diode means for receiving light scattered from the emitted light and producing a light reception signal indicative of the intensity levels of said scattered light;

an electrocardiogram (ECG) monitor means for detecting ECG information and displaying said ECG information and said light reception signal on a common time-base with said light reception signal; and processing means, receiving said light reception signal and said ECG information, for processing said light reception signal as a function of and synchronized with said ECG information to output pulp oxygenation level information of said tooth, and to determine pulsatile blood flow to determine tooth vitality, said information being based on dynamic intensity levels associated with said scattered light.

13. Apparatus as in claim 12, wherein said housing is a substantially U-shaped packaging made of molded plastic and said sensor includes a removable interior coating for the U-shaped packaging of a material which conforms to the shape of said tooth to provide tight mechanical coupling.

14. Apparatus as in claim 12, wherein said first, second and third light emitting diodes each include a plurality of diode devices in series.

15. A method for measuring a pulp oxygenation level of a tooth and for determining vitality of said tooth, comprising for steps of:

emitting light to said tooth;

sensing light scattered by said tooth;

separating a signal indicative of the sensed light into its component parts;

dividing said component parts of said signal each into an AC and a DC signal;

processing said AC and DC signals to produce information that indicates pulp oxygenation level and vitality of said tooth; and displaying said pulp oxygenation level on a bar graph indicator and said vitality via a pulse indicator.

16. The method of claim 15 further comprising the step of improving output information produced in said processing step by providing an electrocardiogram (ECG) monitor which produces a digital signal corresponding to an R-wave pulse of a patient's ECG and using said digital signal in the processing step.

17. A method as in claim 16, wherein said improving step includes adjusting a length of an averaging interval so as to achieve a predetermined signal-to-noise ratio.

18. A method as in claim 16, wherein said processing step includes determining a synchronization between said signal and information from said ECG monitor.

* * * * *